United States Patent
Han et al.

(10) Patent No.: US 11,371,152 B2
(45) Date of Patent: Jun. 28, 2022

(54) PRODUCT SELECTIVITY FOR CO2 REDUCTION

(71) Applicant: The California Institute of Technology, Pasadena, CA (US)

(72) Inventors: Zhiji Han, Pasadena, CA (US); Ruud Kortlever, Pasadena, CA (US); Hsiang-Yun Chen, Pasadena, CA (US); Jonas C. Peters, Pasadena, CA (US); Theodor Agapie, Pasadena, CA (US); Jorge A. Rosas Hernandez, Pasadena, CA (US); Arnaud A. Thevenon, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 258 days.

(21) Appl. No.: 15/950,150

(22) Filed: Apr. 10, 2018

(65) Prior Publication Data

US 2018/0291515 A1    Oct. 11, 2018

Related U.S. Application Data

(60) Provisional application No. 62/483,776, filed on Apr. 10, 2017.

(51) Int. Cl.
| | | |
|---|---|---|
| C25B 3/25 | (2021.01) | |
| C10G 2/00 | (2006.01) | |
| C07C 1/12 | (2006.01) | |
| C10K 3/00 | (2006.01) | |
| C25B 11/051 | (2021.01) | |
| C25B 11/057 | (2021.01) | |
| C25B 11/075 | (2021.01) | |

(52) U.S. Cl.
CPC ............... *C25B 3/25* (2021.01); *C07C 1/12* (2013.01); *C10G 2/50* (2013.01); *C10K 3/00* (2013.01); *C25B 11/051* (2021.01); *C25B 11/057* (2021.01); *C25B 11/075* (2021.01)

(58) Field of Classification Search
CPC .... C25B 3/04; C25B 3/25; C25B 3/26; C25B 11/051; C25B 11/057; C25B 11/075; C07C 1/12; C10G 2/50; C10K 3/00
See application file for complete search history.

(56) References Cited

U.S. PATENT DOCUMENTS

| | | | | |
|---|---|---|---|---|
| 4,897,167 A | * | 1/1990 | Cook | ............ C25B 3/25 205/291 |
| 2011/0226632 A1 | * | 9/2011 | Cole | ............ C25B 3/04 205/446 |
| 2015/0203977 A1 | * | 7/2015 | Luca | ............ C25B 1/003 204/290.11 |
| 2017/0073825 A1 | * | 3/2017 | Sugano | ............ C25B 11/0473 |

FOREIGN PATENT DOCUMENTS

FR    3007426 A1 * 12/2014    ............ B01J 31/123

* cited by examiner

*Primary Examiner* — Ciel P Contreras
(74) *Attorney, Agent, or Firm* — Gavrilovich, Dodd & Lindsey LLP

(57) ABSTRACT

A $CO_2$ reduction system has a cathode in contact with a catholyte. The cathode includes a selectivity-determining layer on an electron conductor. The selectivity-determining layer includes a selectivity-determining component that includes a substituted heterocycle.

19 Claims, 5 Drawing Sheets

| Additive \ Product | Faradaic Efficiency (%) | | | | | | | | | $C_{2+}/CH_4$ | j (mA·cm$^{-2}$) |
|---|---|---|---|---|---|---|---|---|---|---|---|
| | CH4 | C2H4 | C2H5OH | C3H7OH | CO | H2 | HCOO- | $C_{2+}$ | Total | | |
| None | 20.2 | 12.4 | 7.3 | 2.8 | 1.7 | 42.8 | 4.7 | 22.4 | 96.4 | 1.1 | -4.59 |
| 1 | 1.1 | 40.7 | 30.5 | 10.0 | 1.0 | 18.1 | 7.1 | 80.2 | 107.8 | 73 | -1.02 |
| 2 | 0.0 | 4.3 | 5.6 | 0.00 | 0.2 | 62.5 | 6.5 | 9.9 | 87.1 | | -4.14 |
| 3 | 3.1 | 29.3 | 29.6 | 0 | 2.5 | 21.8 | 10.1 | 58.9 | 96.4 | 19 | -0.70 |
| 4 | 0.3 | 37.7 | 22.3 | 8.7 | 2.1 | 16.6 | 10.6 | 68.6 | 98.3 | 229 | -1.46 |
| 5 | 0.1 | 40.8 | 26.7 | 8.6 | 2.1 | 12.4 | 8.8 | 76.1 | 98.5 | 762 | -1.34 |
| 6 | 2.1 | 18.2 | 16.0 | 0 | 3.7 | 52.1 | 6.9 | 34.2 | 99.9 | 16 | -1.40 |
| 7 | 0.07 | 33.5 | 27.1 | 11.8 | 3.1 | 10.0 | 13.0 | 72.4 | 98.7 | 1034 | -1.10 |
| 8 | 5.1 | 1.7 | 0 | 5.3 | 2.6 | 50.5 | 10.6 | 7.0 | 75.8 | 1.4 | -3.32 |
| 9 | 1.5 | 1.2 | 5.1 | 13.9 | 0.4 | 71.0 | 12.4 | 20.2 | 105.5 | 13.3 | -7.49 |
| 10 | 0.4 | 0.1 | 0 | 2.1 | 0.4 | 88.5 | 5.6 | 2.2 | 97.1 | 5.5 | -6.28 |
| 11 | 0.04 | 0 | 0 | 0 | 0.2 | 65.9 | 9.5 | 0 | 75.6 | 0 | -2.95 |
| 12 | 0 | 3.2 | 0 | 0 | 0.7 | 28.6 | 9.0 | 3.2 | 41.5 | | -0.97 |
| 13 | 4.2 | 4.0 | 0 | 0 | 0.3 | 61.6 | 5.5 | 4.0 | 79.6 | 0.95 | -4.03 |
| 14 | 0.01 | 0.07 | 0 | 0 | 0.5 | 78.6 | 1.3 | 0.07 | 78.5 | 7 | -6.44 |
| 15 | 0.2 | 0.01 | 0 | 0 | 0.3 | 91.3 | 5.5 | 0.01 | 97.1 | 0.05 | -4.20 |
| 16 | 0 | 0.2 | 10.0 | 6.0 | 0.1 | 99.3 | 0 | 16.1 | 106.6 | | -12.5 |
| 17 | 0.07 | 34.9 | 16.3 | 6.0 | 1.1 | 23.9 | 12.4 | 57.1 | 94.6 | 1220 | -1.40 |
| 18 | 0.06 | 17.3 | 20.0 | 20.0 | 3.0 | 27.7 | 8.2 | 57.3 | 95.7 | | -2.85 |
| 19 | 0.05 | 45.4 | 14.6 | 3.6 | 0.7 | 19.5 | 6.3 | 63.6 | 92.6 | 1272 | -3.83 |
| 20 | 0.06 | 14.8 | 0 | 0 | 10.9 | 17.5 | 20.6 | 14.8 | 57.5 | 246 | -1.39 |
| 21 | 0.12 | 10.41 | 0.00 | 0.00 | 1.30 | 70.22 | 0.12 | 10.4 | 97.5 | 87 | -2.72 |
| 22 | 0 | 0 | 0 | 0 | 0.02 | 97.1 | 0.4 | 0 | 97.4 | | -17.4 |

Figure 4A

| Additive \ Product | Faradaic Efficiency (%) | | | | | | | | | $C_{2+}/CH_4$ | j (mA·cm$^{-2}$) |
|---|---|---|---|---|---|---|---|---|---|---|---|
| | CH4 | C2H4 | C2H5OH | C3H7OH | CO | H2 | HCOO- | $C_{2+}$ | Total | | |
| 17 | 0 | 35.3 | 18.5 | 0 | 0.1 | 35.0 | 12.9 | 53.8 | 101.8 | | -3.30 |
| 19 | 0.4 | 41.2 | 21.6 | 2.0 | 0.4 | 23.9 | 1.8 | 64.8 | 95.3 | 161 | -1.02 |

Figure 4B

PRODUCT SELECTIVITY FOR CO2 REDUCTION

RELATED APPLICATION

This Application claims the benefit of U.S. Provisional Patent Application Ser. No. 62/483,776, filed on Apr. 10, 2017, and incorporated herein in its entirety.

STATEMENT REGARDING FEDERALLY SPONSORED RESEARCH

This invention was made with government support under Grant No. DE-SC0004993 awarded by the Energy Office of Science of the U.S. Department of Energy. The government has certain rights in the invention.

FIELD OF THE INVENTION

The present invention relates to $CO_2$ reduction, and more particularly, to selectivity of products in $CO_2$ reduction.

BACKGROUND

The $CO_2$ reduction reaction is of particular interest for generating multicarbon products for use as fuels, chemical precursors for industrial applications and other applications. For instance, the $CO_2$ reduction reaction can generate $C_{\geq 2}$ hydrocarbons for use as fuels. Additionally, the $CO_2$ reduction reaction can occur at the cathode of a solar fuels generator. As a result, the $CO_2$ reduction reaction may be useful in renewable energy technologies.

In addition to $C_{\geq 2}$ hydrocarbons, the $CO_2$ reduction reaction can produce a variety of products in addition to $C_{\geq 2}$ hydrocarbons. For instance, the $CO_2$ reduction reaction can produce methane in addition to $C_{\geq 2}$ hydrocarbons or as an alternative to $C_{\geq 2}$ hydrocarbons. Additionally, the hydrogen evolution reaction (HER) can also occur under the same conditions as the $CO_2$ reduction reaction. Accordingly, there is a need to control the selectivity of the $CO_2$ reduction reaction for particular products.

SUMMARY

A $CO_2$ reduction system has a cathode in contact with a catholyte. The cathode includes a selectivity-determining layer on an electron conductor. The selectivity-determining layer includes a selectivity-determining component that includes a substituted heterocycle.

Another embodiment of $CO_2$ reduction system includes a cathode in contact with a catholyte. The catholyte includes an additive that has a substituted heterocycle.

A method of reducing $CO_2$ includes reducing an additive included in a catholyte that contacts a cathode that includes an electron conductor. The additive is reduced so as to generate a reduced additive. The method also includes processing the reduced additive so as to generate a selectivity component. The selectivity component is generated by dimerizing the reduced additive, oligomerizing the reduced additive, and/or polymerizing the reduced additive. Processing the reduced additive forms a selectivity-determining layer on the electron conductor such that the selectivity-determining layer includes the selectivity component.

BRIEF DESCRIPTION OF THE FIGURES

FIG. 4A is a table of experimental results showing a profile of $CO_2$ reduction products produced by electrolysis of catholytes having different additives.

FIG. 4B is a table of experimental results showing a profile of $CO_2$ reduction products produced by electrolysis of catholytes having different additives.

DESCRIPTION

Figures 1, 2:
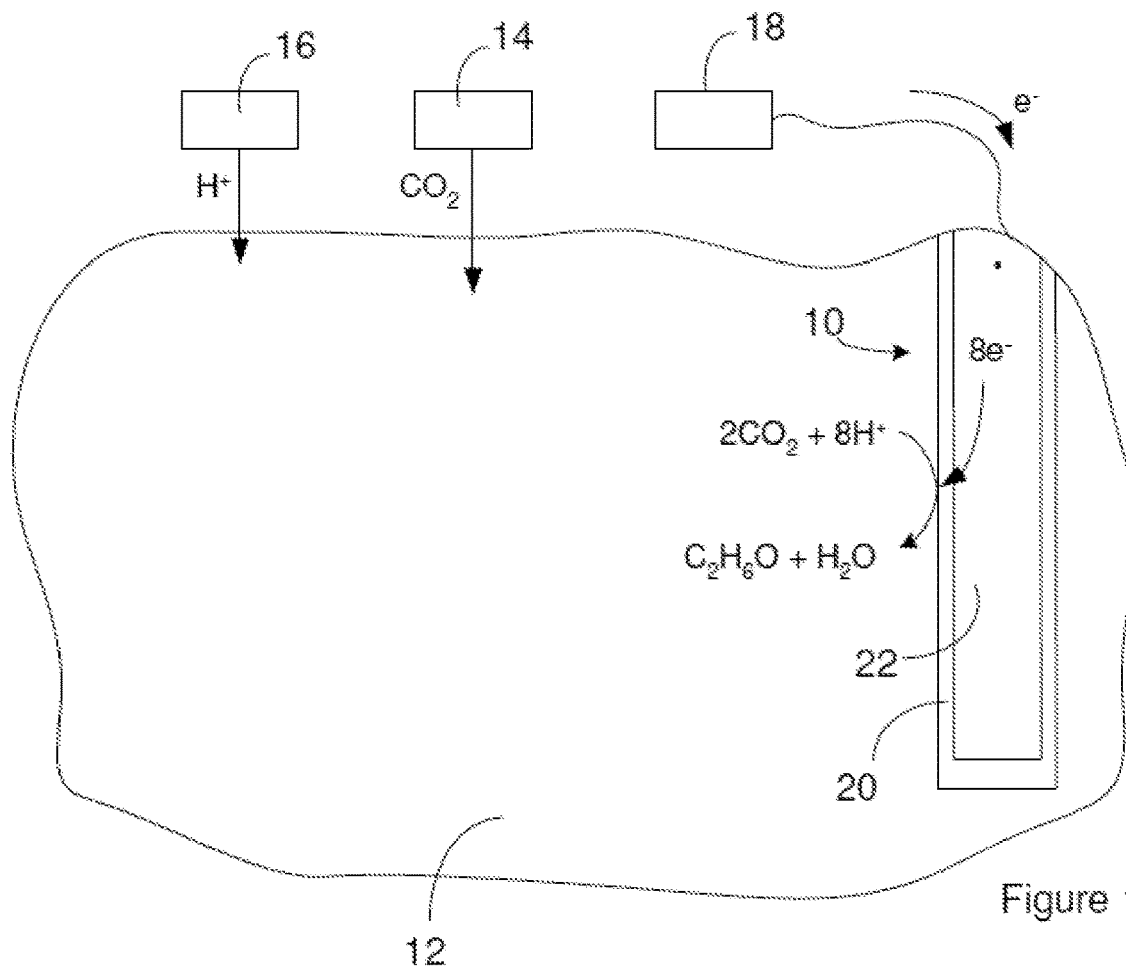
FIG. 1 is a schematic of a $CO_2$ reduction system.
FIG. 2 is a table of experimental results showing a profile of $CO_2$ reduction products produced by electrolysis of catholytes having different concentrations of an additive in a catholyte.

As used herein and in the appended claims, the singular forms "a," "an," and "the" include plural referents unless the context clearly dictates otherwise. Thus, for example, reference to "an additive" includes a plurality of additives and reference to "the catholyte" includes reference to one or more catholytes and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

Also, the use of "and" means "and/or" unless stated otherwise. Similarly, "comprise," "comprises," "comprising" "include," "includes," and "including" are interchangeable and not intended to be limiting.

A $CO_2$ reduction system includes a catholyte in contact with a cathode. The cathode includes a selectivity component that includes a substituted heterocycle. Operation of the $CO_2$ reduction system can generate a variety of different $CO_2$ reduction products. However, the profile of $CO_2$ reduction products that is produced is a function of the substituents on the heterocycle. For instance, certain substituents have provided a large shift toward $C_{\geq 2}$ hydrocarbons and away from lower order carbons such as methane. For instance, additives having a substituted aryl N-substituted on a pyridinium provide $C_{\geq 2}$ selectivity above 60% and even above 75%. Accordingly, the disclosed $CO_2$ reduction system provides a simple system for shifting the $CO_2$ reduction products to higher carbon number products.

Further, the above selectivity levels are achieved using polycrystalline copper as an electron conductor in the cathode. Prior $CO_2$ reduction systems have used specialized copper materials as the cathode. For instance, prior $CO_2$ reduction systems have used copper with particular crystalline orientations and faces in order to control the profile of the $CO_2$ reduction products. Cathodes using these materials are undesirably expensive. Since these specialized copper materials are not required for the disclosed $CO_2$ reduction system, the disclosed $CO_2$ reduction system reduces the cost of $CO_2$ reduction.

FIG. 1 illustrates a $CO_2$ reduction system. The system includes a cathode 10 in contact with a catholyte 12. The catholyte can be a liquid, solid, or vapor. In some instances, the catholyte includes one or more electrolytes in a solvent or mixture of solvents. Suitable solvents include, but are not limited to, water, acetonitrile, ionic liquids, and methanol. Suitable electrolytes include, but are not limited to, $KHCO_3$, KOH, $NaHCO3$, and NaOH. The catholyte also includes $CO_2$ and protons.

When it is desirable for the $CO_2$ reduction system to operate at or near steady state, the $CO_2$ reduction system can include a $CO_2$ source 14. The $CO_2$ source can be configured to maintain the concentration of $CO_2$ in the catholyte. For instance, the $CO_2$ source can be configured to bubble $CO_2$ through a liquid catholyte. Additionally or alternatively, the $CO_2$ source can maintain a $CO_2$ atmosphere over the catholyte. Other mechanisms for providing $CO_2$ in the catholyte include, but are not limited to, high pressure electrochemical cells and gas diffusion electrodes.

When it is desirable for the $CO_2$ reduction system to operate at steady state, the $CO_2$ reduction system can include a proton source 16. The source of protons in the catholyte can depend on the application of the $CO_2$ reduction system. For instance, the illustrated $CO_2$ reduction system can be incorporated into a variety of different applications such as fuel generators including solar fuels generators. In one example, the cathode and catholyte of FIG. 1 represent the cathode and catholyte of a solar fuels generator that pairs the illustrated $CO_2$ reduction reaction with an oxygen evolution reaction (OER) at the anode. In this example, protons generated by the oxygen evolution reaction (OER) can pass through a separator between the anode and the cathode and serve as the protons in the catholyte.

The $CO_2$ reduction system includes an electron source 18. The electron source can also depend on the application of the $CO_2$ reduction system. For instance, when the illustrated $CO_2$ reduction system is incorporated into a solar fuels generator, the electron source can be a semiconductor that is illuminated so as to generate electron-hole pairs. An electrical pathway between the cathode and the semiconductor can transport the electrons from the semiconductor to the cathode. Other electron sources include, but are not limited to, batteries, grid power, solar energy, wind, and hydropower.

The cathode includes a selectivity-determining layer 20 on an electron conductor 22. In some instances, the selectivity-determining layer 20 is in direct physical contact with the electron conductor 22 and/or is chemically bonded to the electron conductor 22. Suitable electron conductors include copper and other metals that are typically used as cathode materials. However, copper has proven to be one of very few materials capable of converting $CO_2$ to $C_{\geq 2}$ products with significant efficiencies.

During operation of the $CO_2$ reduction system, a potential is applied to the cathode so as to cause the $CO_2$ reduction by electrolysis. Suitable potentials levels include, but are not limited to, levels between $-0.8$ V and $-1.3$ vs. RHE. The potential can be applied by the electron source. The electrons from the cathode react with the $CO_2$ and protons in the catholyte to provide a $CO_2$ reduction product. For the purposes of illustration, the $CO_2$ reduction system is shown producing ethanol; however, the system can produce other products. For instance, the following generalized reaction can represent the reaction at the cathode:

$$MCO_2 + 4PH^+ + 4Pe^- \rightarrow C_M H_{2N} O_{(2M+N-2P)} + (2P-N)H_2O$$

where M, N, and P are non-negative numbers and, in some instances, are integers. $C_M H_2 NO_{(2M+N-2P)}$ represents the $CO_2$ reduction product. Examples of the $CO_2$ reduction product that can be produced using this reaction in combination with a solar fuels generator include carbon monoxide, methanol, methane, ethanol, and formic acid. The following table 1 presents values for M, N and P that can be used to generate a particular $CO_2$ reduction product.

TABLE 1

| M | N | P | Product | Chemical Name |
|---|---|---|---------|---------------|
| 1 | 2 | 2 | CH4 | Methane |
| 2 | 4 | 3 | 2 molecules of $CH_3OH$ produced | Methanol |
| 2 | 2 | 1 | 2 molecules of HCOOH produced | Formic acid |
| 2 | 2 | 2 | $CH_3COOH$ | Acetic Acid |
| 2 | 3 | 3 | $C_2H_6O$ | Ethanol |
| 3 | 3 | 4 | $CH_3CH_2COH$ | Propanol |
| 3 | 4 | 4 | $HOCH_2CH_2CH_2OH$ | 1,3-Propanediol |
| 4 | 3 | 4 | $CH_3CH_2COCOOH$ | 2-Oxybutyric acid |
| 4 | 5 | 6 | $CH_3CH_2CH_2COH$ | Butanol |
| 6 | 6 | 6 | $C_6H_{12}O_6$ | Glucose |

Table 1 shows that a variety of products can result from $CO_2$ reduction; however, many of the higher carbon number $CO_2$ reduction products are desirable for commercial, education, research and other applications such as fuels and precursors for the chemistry industry. Examples of desirable high carbon number $CO_2$ reduction products include, but are not limited to, ethanol, ethylene, isopropanol, and allyl alcohol. The selectivity-determining layer can be constructed to tune the selectivity of the $CO_2$ reduction system for particular $CO_2$ reduction products.

The selectivity-determining layer can include, consist of, or consist essentially of a selectivity-determining component selected from a group consisting of a dimer, an oligomer, and a polymer derived from an organic additive. The selectivity-determining component includes a substituted heterocycle. As a result, the selectivity-determining layer can include or consist of monomers, dimers, oligomers, or polymers that each includes or consists of substituted heterocycles. For instance, the selectivity-determining layer can include or consist of monomers, dimers, oligomers, or polymers formed from additives that each includes or consists of one or more substituted heterocycles.

The selectivity-determining component can be generated from additives included in the catholyte. For instance, the additives can be included in the catholyte and application of the electrical potential to the cathode while it contacts the catholyte can reduce the additive to provide a reduced additive that serves as the selectivity-determining component. Additionally or alternatively, the application of the electrical potential to the cathode while it contacts the catholyte can cause bond formation and/or cleavage in the additive and/or the reduced additive resulting in the generation of new chemical structures, including dimers, oligomers, and/or polymers of the reduced additives. These dimers, oligomers, and/or polymers can serve as the selectivity-determining component. Suitable mechanisms for generating the dimer, oligomer, or polymer from an additive or reduced additive include, but are not limited to, reductive coupling. When the concentration of selectivity-determining component exceeds its solubility, the selectivity-determining component electrodeposits on the electron conductor. This electrodeposition can be concurrent with operation of the $CO_2$ reduction system to produce $CO_2$ reduction products. Accordingly, the selectivity-determining layer may not be present on the electron conductor before or at the start of operating the $CO_2$ reduction system. Alternately, the selectivity-determining layer can be formed on the electron conductor before operation of the $CO_2$ reduction system to produce $CO_2$ reduction products. A suitable concentration for the additives in the catholyte include, but are not limited to, concentrations greater than 1 mM and/or less than 20 mM.

In some instances, the ring structure in the heterocycles includes one or more carbons and one or more components selected from the group consisting of phosphorous, silicon, boron sulfur and nitrogen and sulfur. In some instances, the ring structure in the above heterocycles includes or consists of one or more nitrogens and one or more carbons. The heterocycles include one or more substituents.

A suitable dimer includes repeating units that each includes one or more substituted heterocycles. In some instances, the repeating units are directly linked together at the para position of the substituted heterocycles. An example of a dimer that can serve as a selectivity-determining component can be represented by:

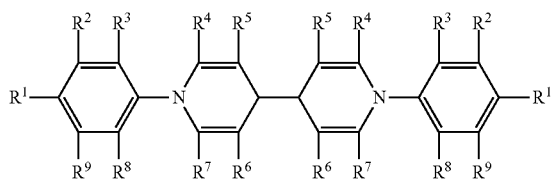

(Formula II) where $R^{1-9}$ can be the same or different and can be H, alkyl groups, aryl groups, hydrocarbyl, halogens, alkoxy, thiol, aminyl groups including primary aminyl and secondary aminyl, phosphorous-containing including phosphine and phosphate, silicon-containing, and boron-containing group including borane, boronic acid and boronic ester. The substituents can be branched or unbranched and/or can include or consist of one or more ring structures. Each of the one or more ring structures in a substituent can be a homocycle or a heterocycle. In some instances, each of the one or more ring structures in a substituent is an unsubstituted aryl group or a substituted aryl group. A substituent including one or more ring structures can have one or more ring in a fused arrangement and/or one or more rings in an unfused arrangement. A ring in a fused arrangement can be fused with the substituted heterocycle or can be fused with one or more other rings in the substituent or in another substituent. The above substituents $R^{1-9}$ can be linked to one another so as to form one or more of the above ring structures. The above substituents $R^{1-9}$ can be saturated or unsaturated and/or halogenated or unhalogenated. A halogenated substituent can be fully or partially halogenated.

The species of Formula II can be generated from additives represented by:

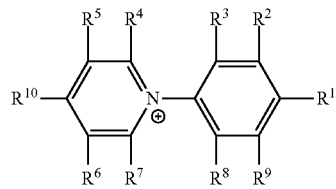

(Formula III) where $R^{1-9}$ are as defined in Formula II and $R^{10}$ is H, alkyl groups, aryl groups, other hydrocarbyl groups, halogens, alkoxy, thiol, aminyl groups including primary aminyl and secondary aminyl, phosphorous-containing groups including phosphine and phosphate, silicon-containing groups, and boron-containing groups including borane, boronic acid and boronic ester. The additive of Formula III includes a substituted pyridinium that includes an N-heterocycle. Additionally, the N-heterocycle is N-substituted with a substituted aryl group (for example, tolyl). When a catholyte includes protons, $CO_2$ and the additive according to Formula III and a potential is applied to the electron conductor in the cathode so as to cause reduction, a selectivity-determining layer that includes or consists of the dimers according to Formula II forms on the electron conductor. Operating the $CO_2$ reduction system so as to provide electrolysis of the catholyte causes the additive of Formula III to reduced and dimerize to the dimer of Formula II by reductive coupling. The dimer of Formula II is not soluble in the catholyte and according deposits on the electron conductor.

The results of operating multiple different $CO_2$ reduction systems with catholytes having different concentrations of the Formula III additive are shown in FIG. 2. The first row of FIG. 2 also shows the results for operating the $CO_2$ reduction system without additives in the catholyte. The presence of the additives in the catholyte provides a surprising shift toward higher carbon number $CO_2$ reduction products ($C_{\geq 2}$ products). For instance, the presence of the additives increases the ratio of $C_{\geq 2}$ products/$CH_4$ increases to over 130 times the ratio that occurs when the additives are not present.

When the selectivity-determining component is an oligomer or polymer, the substituted heterocycles can be included in the backbone and/or sidechains of the oligomer or polymer. In some instances, the repeating units in the polymer or oligomer each includes one or more substituted heterocycles. In some instances, the repeating units and the terminal units in the polymer or oligomer each includes one or more substituted heterocycles. An example of a suitable oligomer or polymer includes multiple substituted heterocycles linked together in the backbone of each of the repeating units. In some instances, the repeating units include a linker that connects nitrogens in the rings of different substituted heterocycles. Another example of a suitable oligomer or polymer includes multiple substituted heterocycles linked together in the backbone of each of the repeating units. In some instances, the repeating units include a linker that connects nitrogens in the rings of different substituted heterocycles and the repeating units are directly linked together at the para position of the substituted heterocycles. The above linkers can include carbon and hydrogen and zero or one or more than one components selected from the group consisting of oxygen, nitrogen, sulfur, phosphorus, boron, and silicon.

Examples of polymers that are suitable for use as the selectivity-determining component and that includes multiple substituted heterocycles included in each repeating unit in the backbone include, but are not limited to, oligomers and polymers represented by:

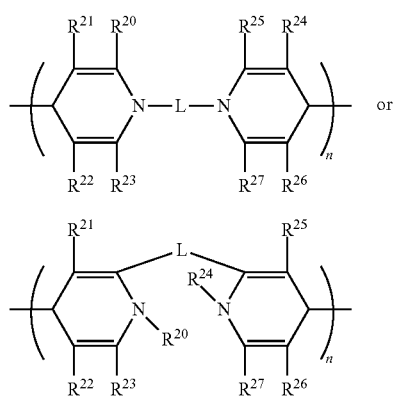

(Formula IVA)

(Formula IVB)

where L represents nil or a linker and n can be greater than or equal to 1. $R^{21-27}$ can be the same or different and can be H, an alkyl groups, aryl groups, hydrocarbyl groups, halogen, alkoxy, thiol, aminyl groups including primary an aminyl groups and secondary aminyl groups, phosphorous-containing groups including phosphine and phosphate, silicon-containing groups, and boron-containing groups including borane, boronic acid and boronic ester. The substituents $R^{21-27}$ can be branched or unbranched and/or can include or consist of one or more ring structures. Each of the one or more ring structures in a substituent can be a homocycle or a heterocycle. In some instances, each of the one or more ring structures in a substituent is an unsubstituted aryl group or a substituted aryl group. A substituent including one or more ring structures can have one or more ring in a fused arrangement and/or one or more rings in an unfused arrangement. A ring in a fused arrangement can be fused with the substituted heterocycle or can be fused with one or more other rings in the substituent or in another substituent. The above substituents $R^{21-27}$ can be linked to one another or to another substituted heterocycle to so as to form one or more of the above ring structures. The above substituents $R^{21-27}$ can be saturated or unsaturated and/or halogenated or unhalogenated. A halogenated substituent can be fully or partially halogenated. In the oligomer or polymer of Formula IVA and Formula IVB, the repeating units are directly linked together at the para position of the substituted heterocycles.

Suitable linkers for use in the oligomer or polymer of Formula IVA and Formula IVB include, but are not limited to, organic linkers, alkyl groups, aryl groups, hydrocarbyl groups, thiol, aminyl groups, phosphorous-containing groups, silicon-containing groups, and boron-containing groups. In some instances, the organic linker includes carbon and hydrogen and zero, one, or more than one component selected from the group consisting of oxygen, nitrogen, sulfur, phosphorus, carbon and boron. Examples of suitable organic linkers include, but are not limited to, alkylene, alkylene oxide, bivalent ether moieties, arylenes. The linker can be branched or unbranched and/or can include or consist of one or more ring structures. Each of the one or more ring structures in a linker can be a homocycle or a heterocycle.

In some instances, each of the one or more ring structures in a linker is an unsubstituted aryl group or a substituted aryl group. A substituent including one or more ring structures can have one or more ring in a fused arrangement and/or one or more rings in an unfused arrangement. A ring in a fused arrangement can be fused with the substituted heterocycle or can be fused with one or more other rings in the substituent or in another substituent. The above linker can be saturated or unsaturated and/or halogenated or unhalogenated. These linkers can be substituted or unsubstituted. The above linkers can be completely or partially halogenated.

Suitable additives for forming oligomers and/or polymers include one or more substituted heterocycles. In some instances, the repeating units and the terminal units in the polymer or oligomer each includes one or more substituted heterocycles that are susceptible to reduction at the anode. For instance, the substituted heterocycles can include pyridinium, imidazolium, and other electron deficient heterocycles, substituted or not. An example of a suitable additive includes multiple substituted heterocyles linked together. In some instances, the additive includes a linker that connects nitrogens in the rings of different substituted heterocycles. Another example of a suitable additive includes a linker that connects nitrogens in the rings of different substituted heterocycles.

An example of an additives from which the compound of Formula IVA and Formula IVB can be generated can be represented by:

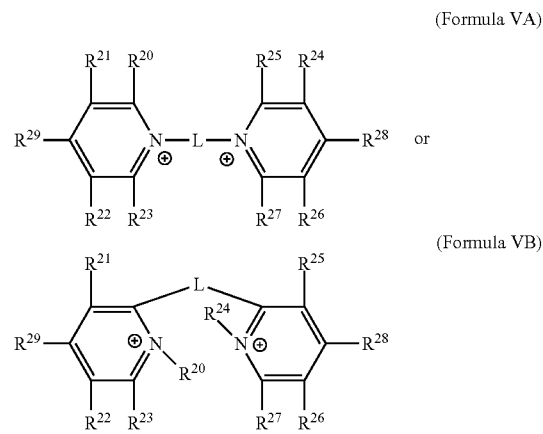

(Formula VA)

(Formula VB)

where L represents nil or the linker of (Formula IVA or Formula IVB), the substituents $R^{21-27}$ correspond to Formula IVA and Formula IVB, $R^{28}$ represents an H, alkyl group, aryl group, hydrocarbyl group, halogen, alkoxy, thiol, aminyl group including a primary aminyl and secondary aminyl, a phosphorous-containing group including phosphine and phosphate, a silicon-containing group, and a boron-containing group including borane, boronic acid or boronic ester. $R^{29}$ represents an H, alkyl group, aryl group, hydrocarbyl group, halogen, alkoxy, thiol, aminyl group including a primary aminyl and secondary aminyl, a phosphorous-containing group including phosphine and phosphate, a silicon-containing group, and a boron-containing group including borane, boronic acid or boronic ester. Operating the $CO_2$ reduction system so as to cause reductive coupling causes the additive of Formula VA and Formula VB to oligomerize or polymerize to the oligomer or polymer of Formula IVA or Formula IVB. Operating the $CO_2$ reduction system so as to cause reductive coupling can be concurrent with or separate from operating the $CO_2$ reduction system so as to reduce $CO_2$. The oligomer or polymer of Formula IVA and Formula IVB is not soluble in the catholyte and according deposits on the electron conductor.

The selectivity provided by the selectivity-determining layer can be tuned by changing the one or more substituents on the substituted heterocyclic additives and accordingly on the resulting monomers, dimers, oligomers, or polymers. Suitable substituents include, but are not limited to, alkyl groups, aryl groups, hydrocarbyl groups, halogens, alkoxy groups, thiols, aminyl groups including primary aminyl groups and secondary aminyl groups, phosphorous-containing groups including phosphine and phosphate, silicon-containing groups, and boron-containing groups including borane, boronic acid and boronic ester. The substituents can be branched or unbranched and/or can include or consist of one or more ring structures. Each of the one or more ring structures in a substituent can be a homocycle or a heterocycle. In some instances, each of the one or more ring structures in a substituent is an unsubstituted aryl group or a substituted aryl group. A substituent including one or more ring structures can have one or more ring in a fused arrangement and/or one or more rings in an unfused arrangement. A ring in a fused arrangement can be fused with the substituted heterocycle or can be fused with one or more other rings in the substituent or in another substituent. The above substituents can be saturated or unsaturated and/or halogenated or unhalogenated. A halogenated substituent can be fully or partially halogenated.

When the substituted heterocycle includes one or more nitrogens in the ring, all or a portion of the one or more substituents can each be linked to one or more of the nitrogens. When the ring structure in the heterocycles includes one or more carbons, all or a portion of the one or more substituents can each be linked to one or more of the carbons. When the ring structure in the heterocycles includes or consists of one or more carbons and one or more nitrogens, a first portion of the one or more substituents can each be linked to a carbon and a second portion of the one or more substituents can each be linked to a nitrogen. When the substituted heterocycle is a substituted pyridine or substituted pyridine ion, one or more of the carbon in the pyridine ring can be linked to a substituent and/or the nitrogen in the pyridine ring can be linked to a substituent. In some instances, the substituted heterocycle is a pyridine or pyridine ion and a substituent is linked to the carbon in the para position in the pyridine ring and/or a substituent is linked to the nitrogen in the pyridine ring.

An example of suitable additives can be represented by:

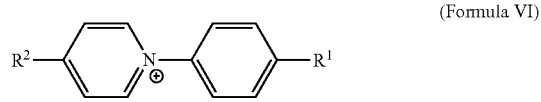

(Formula VI)

In Formula VI, $R^1$ represents H, an alkyl group, aryl group, hydrocarbyl group, halogen, alkoxy group, thiol, aminyl group including primary aminyl groups and secondary aminyl groups, a phosphorous-containing group including phosphine and phosphate, a silicon-containing group, and a boron-containing group including borane, boronic acid and boronic ester. $R^2$ represents H, an alkyl group, aryl group, hydrocarbyl group, halogen, alkoxy group, thiol, aminyl group including primary aminyl groups and secondary aminyl groups, a phosphorous-containing group including phosphine and phosphate, a silicon-containing group, and a boron-containing group including borane, boronic acid and boronic ester. The substituents represented by $R^1$ and/or $R^2$ can be branched or unbranched and/or can include or consist of one or more ring structures. Each of the one or more ring structures in $R^1$ and/or $R^2$ can be a homocycle or a heterocycle. In some instances, each of the one or more ring structures in a substituent is an unsubstituted aryl group or a substituted aryl group. $R^1$ and/or $R^2$ can be saturated or unsaturated and/or halogenated or unhalogenated. A halogenated substituent can be fully or partially halogenated.

Figure 3A:
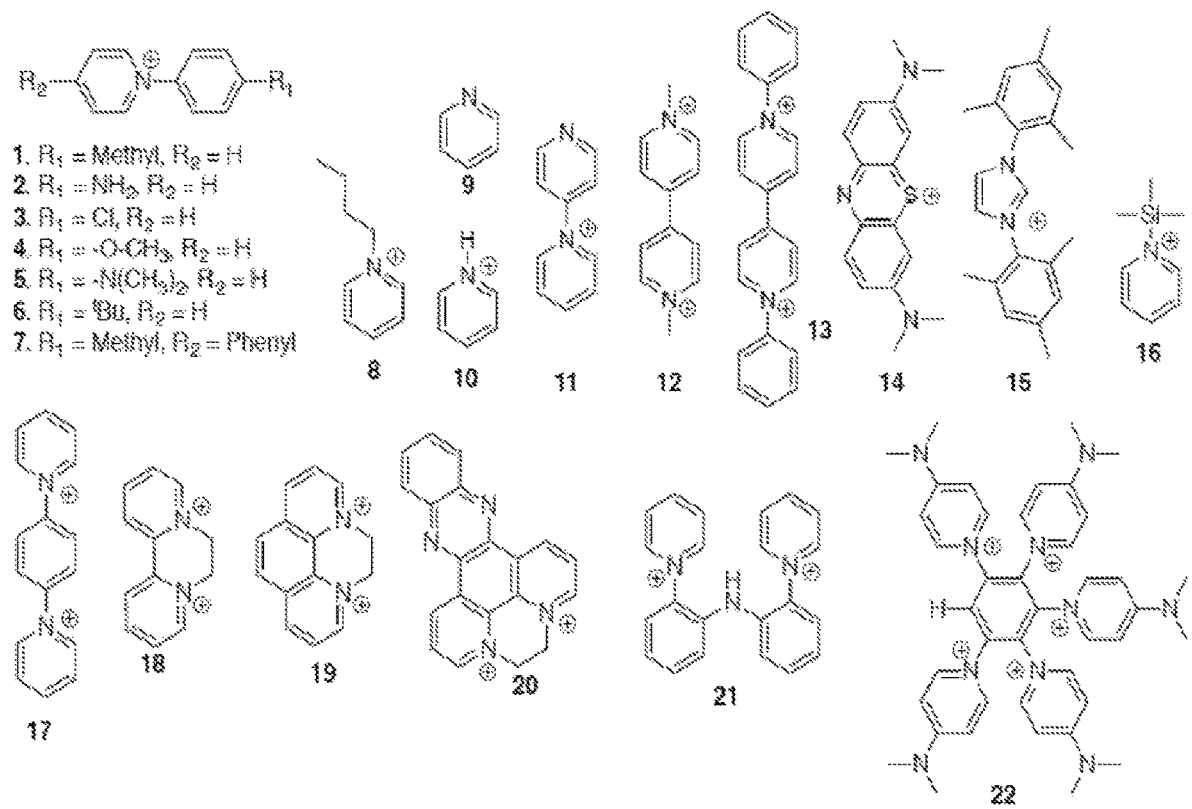
FIG. 3A shows a variety of different additives for use in the catholyte of $CO_2$ reduction system.

FIG. 3A presents additives having a variety of different substituents that each includes a heterocycle. Additives 1-7 are each an example of an additive according to Formula VI. Additives 1-8 and 10-13 each includes one or more substituted pyridine rings or substituted pyridine ion rings as the substituted heterocycle. Additive 14 includes sulfur in the ring of the substituted heterocycle. Additive 15 includes two nitrogens in the ring of the substituted heterocycle. Additives 11-13 include more than one substituted heterocycle structures. The illustrated substituents include branched and unbranched alkyl groups, halogens, substituted and unsubstituted aryl groups, alkoxy groups, and aminyl groups. The substituents of additive 14 have ring structures that are fused with the substituted heterocycle (additive 14). For the purposes of comparison, compound 9 is unsubstituted pyridine.

Additives 17-22 are examples of additives according to Formula VA and accordingly provide a selectivity component that includes an oligomer or polymer. Additive 17 illustrates example of Formula VA where the linker includes one or more phenylene group. In additive 17, a single phenylene group serves as the linker. Additives 18-20 also include linkages at the ortho position of the substituted heterocycles so as to provide fused ring systems.

FIG. 4A presents the results of operating different $CO_2$ reduction systems where the different catholytes each included one of the additives shown in FIG. 3A. The first row of FIG. 4A shows the results for operating the $CO_2$ reduction system without additives in the catholyte. FIG. 4A shows that the dependency of the $CO_2$ reduction product profile on the heterocycle substituents. For instance, the catholyte without additive and the catholyte with the unsubstituted heterocycle additive (compound 9) showed about the same $C_{\geq 2}$ selectivity ($C_{\geq 2}$/total), around 20%. In contrast, the additives having a substituted aryl N-substituted on a pyridinium show a large shifts from $C_1$ $CO_2$ reduction products to higher carbon number ($C_{\geq 2}$) $CO_2$ reduction products. For instance, positively charged additives having a substituted aryl N-substituted on a pyridinium provide $C_{\geq 2}$ selectivity above 60% and even above 75%. Additionally, additives having a substituted aryl N-substituted on a pyridinium can give a ratio of $C_{\geq 2}$ products/$CH_4$ over 500.

In FIG. 4A, the additives that provide oligomeric and/or polymeric selectivity-determining components show similar high selectivity for $C_{\geq 2}$ products ($C_{\geq 2}$ selectivity >60%) but a higher current density. For instance, additive 19 provides a $C_{\geq 2}$ selectivity of 65% and a current up to 7 times higher than additive 1.

Figure 3B:
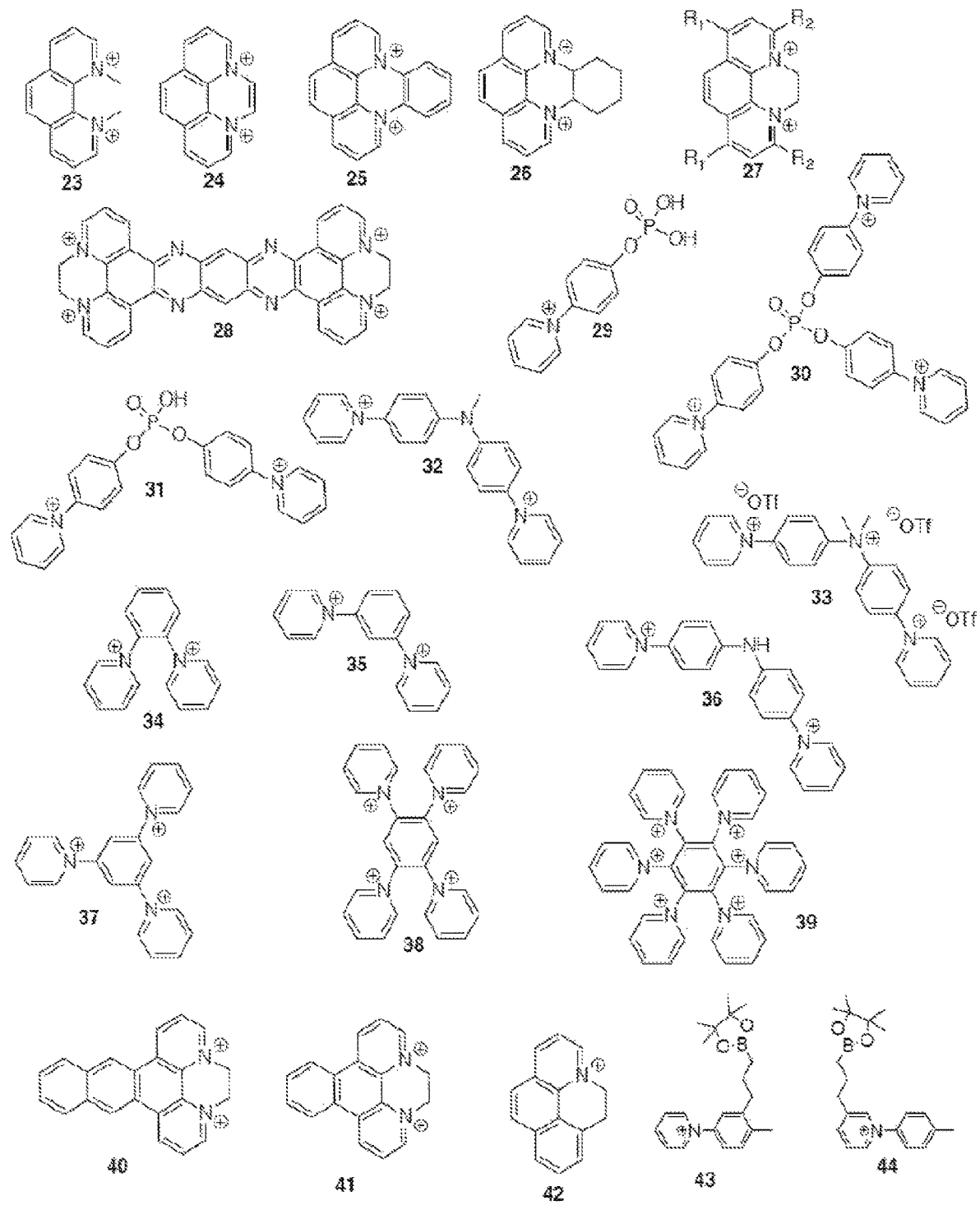
FIG. 3B shows a variety of different additives for use in the catholyte of $CO_2$ reduction system.

FIG. 3B sets forth additional additives according to the disclosure. Additive 22 is an example of an additive according to Formula VB. Additives 22-25, 28-40, 43 are examples of an additive according to Formula VA and/or Formula VB. Additives 26, 27, 41, 42 are examples of additives according to Formula III.

The additives need not be present in the catholyte for the selectivity-determining layer to provide the desired product selectivity. As a result, the presence of the additives in the catholyte is optional. For instance, the selectivity-determining layer can be formed on the electron conductor and then the resulting electrode can be used in a $CO_2$ reduction system where the catholyte excludes the additives. When the catholyte does include the additives, experimental results have shown that the consumption of the additives during $CO_2$ reduction is minimal and corresponds to the material converted to a film on the electrode. For instance, the additive reduction can occur within 5 min.

EXAMPLES

Example 1

$CO_2$ reduction systems were generated according to FIG. 1. Each of the $CO_2$ reduction systems included a cathode having polycrystalline copper as the electron conductor. Different $CO_2$ reduction systems included different catholytes. Each catholyte included N-tolyl Pyridinium additive in 0.1 M $KHCO_3$ saturated with $CO_2$. Different catholytes had a different concentration of N-tolyl Pyridinium additive (0, 1, 5, 10 and 20 mM). Electrolysis was then performed on each of the $CO_2$ reduction systems at different potentials (between −0.8 V to −1.3 V vs RHE) applied to the cathode. The Faradaic efficiency at which different $CO_2$ reduction products were generated during operation of the $CO_2$ reduction system was measured by GC, HPLC and NMR spectroscopy techniques and the results presented in FIG. 2.

Example 2

$CO_2$ reduction systems were generated according to FIG. 1. Each of the $CO_2$ reduction systems included a cathode having polycrystalline copper as the electron conductor. Different $CO_2$ reduction systems included different catholytes. Each catholyte included 10 mM of one of the additives shown in FIG. 3A in 0.1 M $KHCO_3$ saturated with $CO_2$. Electrolysis was then performed on each of the $CO_2$ reduction systems at different over potential (between −0.8 V to −1.3 V vs RHE) applied to the cathode. These experiments were done a −1.1 V vs. RHE. The Faradaic Efficiency at which different $CO_2$ reduction products were generated during operation of the $CO_2$ reduction system was measured by GC, HPLC and NMR spectroscopy techniques and the results presented in FIG. 4A.

Example 3

$CO_2$ reduction systems were generated according to FIG. 1. Each of the $CO_2$ reduction systems included a cathode having polycrystalline copper as the electron conductor. Different $CO_2$ reduction systems included different catholytes. One catholyte included 10 mM of additive 17 from FIG. 3A in 0.1 M $KHCO_3$ saturated with $CO_2$. Another catholyte included 10 mM of additive 19 from FIG. 3A in 0.1 M $KHCO_3$ saturated with $CO_2$. Electrolysis was then performed on each of the $CO_2$ reduction systems at different over potential (between −0.8 V to −1.3 V vs RHE) applied to the cathode. These experiments were done at 1.15 V vs. RHE. The Faradaic Efficiency at which different $CO_2$ reduction products were generated during operation of the $CO_2$ reduction system was measured by GC, HPLC and NMR spectroscopy techniques and the results presented in FIG. 4A. A comparison of FIG. 4A with FIG. 4B shows an example of enhancement of the current density in presence of two additives (17 and 19) when a higher overpotential is applied. Accordingly, the high selectivity for $C_{\geq 2}$ products is retained under these conditions (>60%).

Example 4

A $CO_2$ reduction system was generated according to FIG. 1. The $CO_2$ reduction system included a cathode having polycrystalline copper as the electron conductor. The catholyte included 10 mM of an additive according to Formula III (N-tolyl Pyridinium, compound 1) in 0.1 M $KHCO_3$ saturated with $CO_2$. Electrolysis was then performed for one hour on the $CO_2$ reduction systems with a potential of −1.1 V vs RHE applied to the cathode. An $^1H$ NMR analysis performed on the remaining catholyte showed that over 98% of the additive remained in the catholyte.

Example 5

The Example 1 test performed on the catholyte including the N-tolyl Pyridinium additive (compound) formed a film on the electron conductor. The film was dissolved in organic solvents, rinsed with water and quickly transferred to inert atmosphere where the result was characterized by NMR spectroscopy in $CD_2Cl_2$. The $^1H$ NMR spectrum shows the same number of peaks as N-tolyl pyridinium, but two are shifted significantly upfield. The solid-state structure of this compound was determined by single crystal X-ray diffraction (XRD). The C—C distances within the nitrogen containing ring are indicative of localization of single and double bond character resulted from dearomatization. The structure corresponds to two equivalents of N-tolyl pyridinium being reductively coupled at the para position on pyridine ring, a one-electron reduction per molecule of additive. These results show the dimerization of the additive of Formula III (N-tolyl Pyridinium) so as to provide the dimer of Formula II. Additionally, the mass of the selectivity layer corresponded to only ~1% of the N-tolyl pyridinium originally in the catholyte, accounting for a minor level (~0.6%) of reducing equivalents used in the electrolysis.

Example 6

A $CO_2$ reduction system was generated according to FIG. 1. The $CO_2$ reduction system included a cathode having polycrystalline copper as the electron conductor. The catholyte included 10 mM of an additive according to Formula III (N-tolyl Pyridinium, compound 1) in 0.1 M $KHCO_3$ saturated with $CO_2$. Electrolysis was then performed for one hour on the $CO_2$ reduction systems with a potential of −1.1 V vs RHE applied to the cathode. The catholyte was then replaced by a second catholyte free of N-tolyl Pyridinium and electrolysis was performed for another hour. A similar $CO_2$ reduction product profile was observed for the second hour of electrolysis as was observed for the first hour of electrolysis indicating that the additive in the catholyte is not required for the observed shift in the profile of the $CO_2$ reduction products.

Example 7

A selectivity component according to Formula II was synthesized separately from the $CO_2$ reduction system and then drop cast onto a polycrystalline copper electrode conductor. A $CO_2$ reduction system was generated having the resulting cathode in contact with a catholyte in 0.1 M $KHCO_3$ saturated with $CO_2$. Electrolysis was then performed for one hour on the $CO_2$ reduction systems with a potential of −1.1 V vs RHE applied to the cathode. The profile of the resulting the $CO_2$ reduction products does not result in the same profile observed for the electrodeposited selectivity-determining layers described above indicating that the morphology of the film and/or the nature of the contact between the Cu surface and the layer generated during electrodeposition are instrumental to increased production of $C_{\geq 2}$ species.

Figure 5:
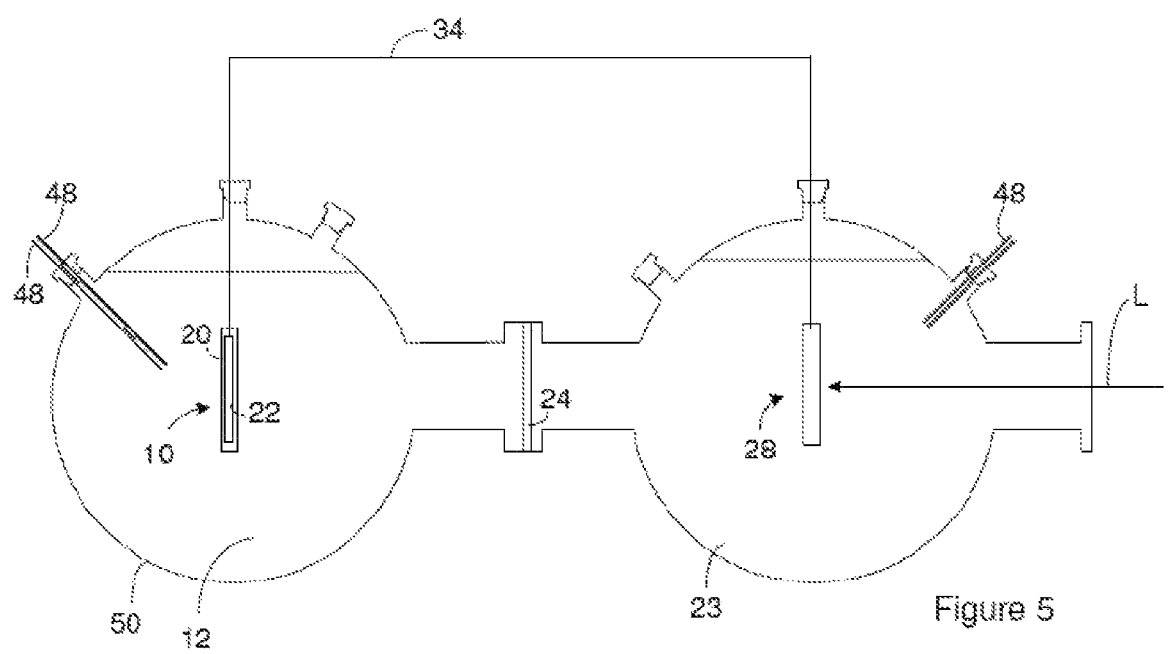
FIG. 5 shows the disclosed $CO_2$ reduction system incorporated into a solar fuels generator.

FIG. 5 shows the disclosed $CO_2$ reduction system incorporated into a solar fuels generator. The solar fuels generator includes the catholyte 12 separated from an anolyte 23 by a separator 24. The anolyte 23 and catholyte 12 each contacts the separator 24. The anolyte 23 can be a solid, liquid, gas, vapor, polymeric electrolytes or a combination thereof. The separator 24 includes ion exchange membrane through which allows protons to pass between the anolyte and catholyte.

One or more electrical conductors 34 provide electrical communication between the anode 28 and the cathode 10. Suitable electrical conductors include, but are not limited to, metal wires, conductive polymers, conductive pastes and combinations thereof. An electrical pathway includes the anode 28, the one or more electrical conductors 34 and the cathode 10.

The anode 28 can be configured to act as an electron source. For instance, the anode 28 can be a photoanode that converts incident light into excited electron-hole pairs that drive the chemical reaction. For instance, the anode can include or consist of a photoanode light absorber selected to absorb light at a wavelength to which the photoanodes 28 will be exposed during operation of the solar fuels generator.

Suitable materials for the photoanode light absorbers include, but are not limited to, semiconductors. In some instances, the photoanode light absorbers include or consist of one or more semiconductors. Suitable semiconductors for the photoanode light absorbers include, but are not limited to, metal oxides, oxynitrides, sulfides, and phosphides that are stable in an oxidizing environment such as WO3, TiO2, and TaON.

In some instances, the photoanode light absorbers are doped. For instance, a photoanode light absorber can be an n-type semiconductor. One or more pn junctions can also be present within a photoanode light absorber and can be arranged so that electrons flow from the anode 28 to an anode catalyst (not shown).

One or more conduits 48 extend into an interior of a catholyte reservoir 50. Each conduit can terminate in the catholyte or above the catholyte. One or more conduits 48 can serve as a $CO_2$ source during operation of the solar fuels generator.

During operation of a solar fuels generator according to FIG. 5, the anode 28 is illuminated as shown by the arrow labeled L in FIG. 1. The photoanode light absorber absorbs at least a portion of the incident light. The absorption of light within the photoanode light absorber excites hole electron pairs within the photoanode light absorber. The position of an n type photoanode light absorber in the anolyte 23 produces an electrical field that causes the holes to move to the surface of the photoanode light absorber and then the surface of the anode catalyst where oxidation of water in the first phase occurs so at to generate protons in the anolyte. The protons can pass through the separator to the catholyte. The electrical field at the anode 28 also causes the electrons that were excited in the anode 28 to move along the electrical pathway 34 to the cathode where the electrons react with $CO_2$ and protons in the catholyte 12 to form the $CO_2$ reduction products.

The disclosed $CO_2$ reduction system is not limited to solar fuels generator applications. For instance, the disclosed $CO_2$ reduction system can be in applications such as industrial or laboratory scale generation of chemicals and chemical precursors.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

The invention claimed is:

1. A CO2 reduction system, comprising:
a cathode in contact with a catholyte,
the cathode including a selectivity-determining layer electrodeposited on an electron conductor, the selectivity-determining layer including a selectivity-determining component that includes a backbone of substituted heterocyle, and
the catholyte includes CO2, an additive and a reduced from of the additive forming the selectivity-determining component,
wherein the CO2 is reduced at the cathode and wherein the selectivity determining component is simultaneously electrodeposited.

2. The system of claim 1, wherein the substituted heterocycle includes one or more nitrogens in a ring structure.

3. The system of claim 1, wherein a substituent on the substituted heterocycle includes an aryl group.

4. The system of claim 3, wherein the aryl group is substituted.

5. The system of claim 1, wherein the additive is positively charged.

6. The system of claim 1, wherein the selectivity-determining component is selected from a group consisting of a dimer, an oligomer, and a polymer.

7. The system of claim 1, wherein the substituted heterocycle is one of multiple substituted heterocycles included in the selectivity-determining component and the selectivity-determining component includes multiple units that each includes one or more of the substituted heterocycles.

8. The system of claim 7, wherein the selectivity-determining component is represented by:

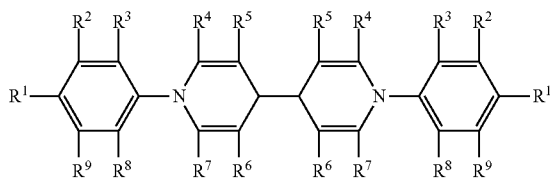

where different portions of $R^{1-9}$ are the same or different and individually represent an H, an alkyl group, an aryl group, a hydrocarbyl group, a halogen, an alkoxy group, a thiol, an aminyl group, a phosphorous-containing group, a silicon-containing group, and a boron-containing group.

9. The system of claim 6, wherein the selectivity-determining component is represented by:

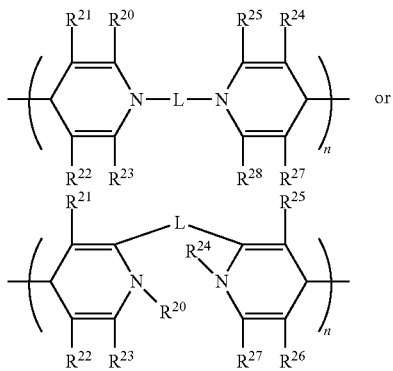

or where L represents nil or an organic linker, n is greater than or equal to 1, $R^{21-27}$ individually represent an H, alkyl group, aryl group, hydrocarbyl group, halogen, alkoxy group, thiol, aminyl group, phosphorous-containing group, silicon-containing group, and a boron-containing group.

10. The system of claim 1, wherein the catholyte includes the additive that can be reduced from which the selectivity-determining component can be formed by electrodeposition.

11. The system of claim 10, wherein the additive is positively charged.

12. The system of claim 11, wherein the additive is represented by

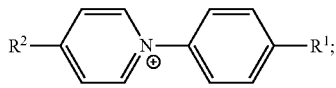

wherein $R^1$ represents an H, alkyl group, aryl group, hydrocarbyl group, halogen, alkoxy group, thiol, aminyl group, phosphorous-containing group, silicon-containing group, and a boron-containing group and $R^2$ represents an H, alkyl group, aryl group, hydrocarbyl group, halogen, alkoxy group, thiol, aminyl group, phosphorous-containing group, silicon-containing group, and a boron-containing group and.

13. A $CO_2$ reduction system, comprising:
a cathode in contact with a catholyte,
the catholyte including $CO_2$ and an additive, the additive including a positively charged substituted heterocycle; and
the cathode comprising a polymeric layer comprising a backbone of substituted heterocycles obtained from a reduced form of the additive.

14. The system of claim 13, wherein the substituted heterocycle includes one or more nitrogens in a ring structure.

15. The system of claim 14, wherein the substituted heterocycle includes a substituent linked to one of the nitrogens in the ring structure.

16. The system of claim 15, wherein the substituent includes an aryl.

17. A method of reducing $CO_2$, comprising:
reducing an additive included in a catholyte in contact with a cathode that includes an electron conductor, the additive being reduced so as to generate a reduced additive,
processing the reduced additive so as to generate a selectivity component, processing the reduced additive includes dimerizing the reduced additive so as to generate the selectivity component, oligomerizing the reduced additive so as to generate the selectivity component, and/or polymerizing the reduced additive so as to generate the selectivity component, and
forming a selectivity-determining layer on the electron conductor, the selectivity-determining layer including the selectivity component while simultaneously reducing $CO_2$ at the cathode.

18. The method of claim 17, wherein the electron conductor is polycrystalline copper.

19. The method of claim 17, further comprising:
reducing the $CO_2$ at the cathode so as to generate multiple different $CO_2$ reduction products that is more than 70% $C_{\geq 2}$.

* * * * *